United States Patent [19]
Imran

[11] Patent Number: 5,817,126
[45] Date of Patent: Oct. 6, 1998

[54] COMPOUND STENT

[75] Inventor: Mir A. Imran, Los Altos Hills, Calif.

[73] Assignee: Surface Genesis, Inc., Menlo Park, Calif.

[21] Appl. No.: 818,275

[22] Filed: Mar. 17, 1997

[51] Int. Cl.⁶ .............................. A61F 2/04; A61M 29/00
[52] U.S. Cl. .................................. 606/198; 623/1; 623/12
[58] Field of Search ............................... 606/1, 108, 191, 606/194, 195, 198, 200; 623/1, 12

[56] References Cited

U.S. PATENT DOCUMENTS 5,383,892 1/1995 Cardon et al. ................................ 623/1
5,575,818 11/1996 Pinchuk ...................................... 623/1
5,591,198 1/1997 Boyle et al. ............................. 606/108

*Primary Examiner*—Michael Buiz
*Assistant Examiner*—William Lewis
*Attorney, Agent, or Firm*—Flehr Hohbach Test Albritton & Herbert LLP

[57] ABSTRACT

A compound stent is disclosed, which includes a cylindrical member having first and second extremities and having a wall defining a central bore having a longitudinal axis and extending from the proximal extremity to the distal extremity, the cylindrical member having first and second end segments and an intermediate segment adjoining the first and second end segments, the first and second end segments being formed of slotted metal and being movable between contracted and expanded conditions, the intermediate segment being formed of a braided material to impart greater flexibility to the stent along the longitudinal axis. Also, a method for making such a stent is disclosed, which includes steps of providing two complementary tubular pieces, each made up of an expandable stent segment from which a plurality of strands are attached by one end, then axially aligning the two pieces with the two stent segments at opposite ends and the strands between them, and moving the two pieces toward one another so that the longitudinally extending strands attached to the two segments pass one another and interlace to form the braided intermediate segment.

26 Claims, 3 Drawing Sheets

COMPOUND STENT

BACKGROUND OF THE INVENTION

This invention relates to stents and stent grafts for deployment within tubular anatomical structures within the body, for supporting the walls of the structures. Particularly the invention relates to expandable elongate flexible vascular stents and stent grafts.

Expandable stents and stent grafts are known in a wide variety of designs. These devices are made up of various arrangements of struts in a generally cylindrical shape, expandable from a smaller diameter roughly cylindrical configuration (in which certain of the struts are circumferentially more compacted) to a larger diameter roughly cylindrical configuration (in which certain of the struts are circumferentially more spread apart).

Generally, an expandable stent or stent graft is passed into and through the lumen of the tubular structure (such as a blood vessel) in a collapsed (that is, unexpanded) condition until the treatment site is reached, and then the stent or stent graft is caused to expand (or is permitted or induced to expand) to contact and press against the lumenal surface of the wall of the tubular structure at the treatment site.

Where the particular treatment calls for a stent or stent graft of extended length, the device should be sufficiently flexible (at least in the collapsed configuration) to permit negotiation of curves within the vessel during deployment to the treatment site. At the same time, where the stent or stent graft is intended to prevent closure of the lumen of the vessel, the device in the expanded state should have sufficient radial strength to resist restenosis or collapse of the vessel wall.

One approach to providing for a stent graft of extended length and good radial strength is to connect two or more shorter inflexible stent segments in tandem by means of flexible connectors. Such an arrangement is described in co-pending U.S. patent application Ser. No. 08/818,274, titled "Stent", filed Mar. 17, 1997, which patent application is hereby incorporated herein in its entirety by reference. Such an assembly permits flex in the device between the tandemly arranged stent segments; it is not continuously flexible.

Continuously highly flexible grafts in a variety of designs have been proposed, including for example coil springs, tubes of polymeric material (such as PTFE), and woven polymeric tubes (made for example, of a woven polyester such as Dacron). Coil springs are not generally readily expandable. PTFE tubes and woven Dacron tubes, on the other hand, while useful for treatment of aneurism, have insufficient radial strength to be useful for treatment of stenotic disease.

Braided or woven metal tubes can be expanded and can provide good radial strength; but the strands of such braided devices tend to fray at the ends, and this can result in sharp projections or fuzzy ends that can be harmful to surrounding tissues, and can to some extent obstruct flow through the vessel. Moreover, it is desirable for the ends of the stent or graft to be smooth, to provide clean transition at the lumenal surface between the vessel wall and the ends of the graft. As one expedient, not fully satisfactory, the strands at the ends of braided grafts can be welded to reduce fraying.

One example of a treatment in which extended length grafts having substantial radial strength may be useful is a saphenous vein graft; here the condition being treated is a stenotic disease, and so substantial resistive force preventing the collapse of, or stenosis of, the vessel is required. Other vascular treatment sites include by way of example carotid arteries, coronary arteries, and the aorta, particularly where the disease condition is a stenotic one and where it is desired to provide a stent for an extended segment of a vessel.

SUMMARY OF THE INVENTION

The invention provides for a cylindrically shaped expandable compound stent, including expandable stent segments at each end and an extended length expandable intermediate segment in the form of a braid of interlaced strands.

The intermediate segment provides continuous flexibility, and the stent segments provide for easy deployment of the device as well as for clean transitions between the lumenal surface of the vessel wall and the ends of the device.

In some embodiments the intermediate segment is formed of the same material as the first and second segments, and the device provides sufficient radial strength for use in treatments of stenotic disease conditions.

In one general aspect the invention features a compound stent including a cylindrical member having an outside diameter, a length, and first and second extremities, and having a wall defining a central bore having a longitudinal axis and extending from the proximal extremity to the distal extremity, the cylindrical member having first and second end segments and an intermediate segment adjoining the first and second end segments, the first and second end segments being formed of slotted metal and being movable between contracted and expanded conditions, the intermediate segment being formed of a braided material to impart greater flexibility to the stent along the longitudinal axis.

According to the invention, the compound stent can be constructed by making two complementary tubular pieces, each made up of an expandable stent segment from which a plurality of strands are attached by one end, then axially aligning the two pieces with the two stent segments at opposite ends and the strands between them, and moving the two pieces toward one another so that the longitudinally extending strands attached to the two segments pass one another and interlace to form the braided intermediate segment.

In some embodiments the free ends of at least some of the strands are affixed to the complementary piece after the braided intermediate segment has formed.

In a second general aspect, then, the invention features a method for making a compound stent, by steps of providing a first part and a second part, each part having generally cylindrical shape with an outside diameter, a length, and first and second extremities, and having a wall defining a central bore having a longitudinal axis and extending from the first extremity to the second extremity, each part having a stent segment and a strand segment, the stent segment being formed of slotted material and being movable between contracted and expanded conditions, the strand segment including a plurality of strands each of which is connected by one end to the stent segment and has the other end free.

In some embodiments the strand segment and the stent segment are formed of the same slotted material; in preferred embodiments the material is a metal such as a stainless steel, for example 316 stainless or 304 stainless, or a shape memory material such as a nickel-titanium alloy ("nitinol"), or is a plastic such as for example a nylon, or is a composite or laminated material such as for example a platinum/stainless steel laminate or a nitinol/stainless steel laminate or a gold/stainless steel laminate, to provide a combination of materials characteristics.

DESCRIPTION OF PREFERRED EMBODIMENTS

Additional Objects and Features of the Invention will appear from the following description, in which the preferred embodiments are set forth in detail, in conjunction with the accompanying drawings. The drawings are not presented to scale.

Figure 1:
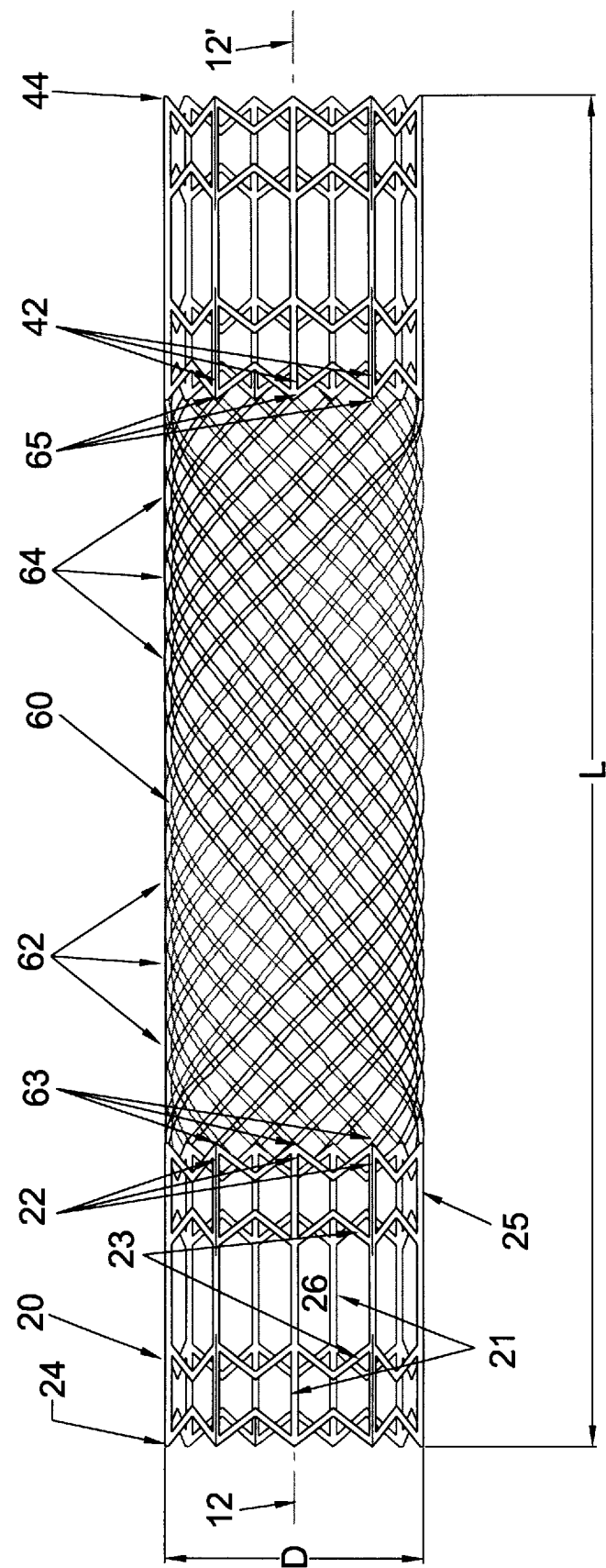

Drawings FIG. 1 is a sketch in a side view, showing a compound stent according to the invention.

Figure 2:
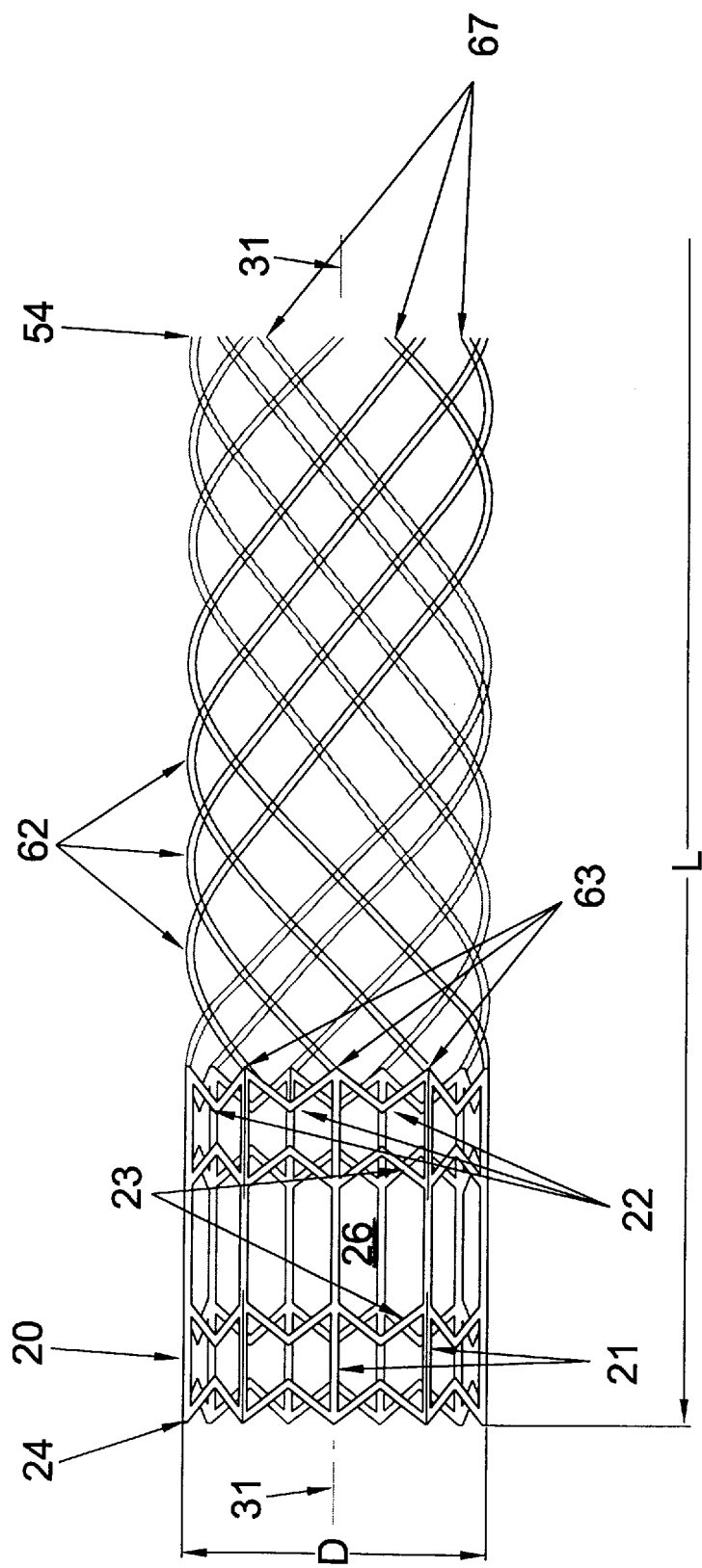
Figure 3:
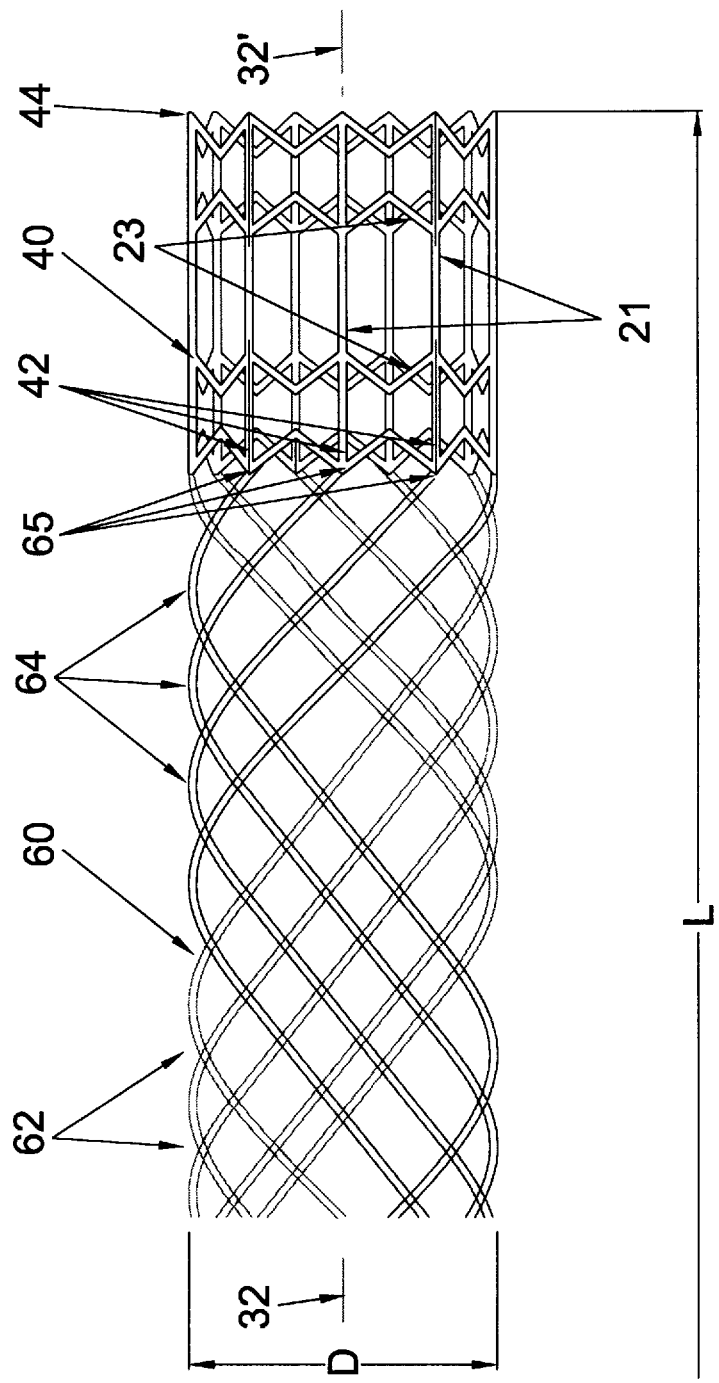

FIGS. 2 and 3 are sketches showing complementary parts of a compound stent according to the invention which, when assembled according to the invention as described in more detail below, form the compound stent of FIG. 1.

Referring now to FIG. 1, a compound stent according to the invention is shown generally at 10 in an expanded condition as if deployed in a vessel (not shown in the Figure). Compound stent 10 includes a generally cylindrical member 11 having an outside diameter represented by the dimension D in FIG. 1 and a length represented by the letter L in FIG. 1, and first and second extremities 24 and 44. The cylindrical member 11 has a wall 25 which defines a central bore 26 having a central longitudinal axis 12–12' and extending from the first extremity 24 to the second extremity 44.

The dimensions of the compound stent differ for different uses. The expanded diameter D, for example, is selected according to the inner diameter of the particular tubular anatomical structure (such as a particular blood vessel) to be treated. For instance, a suitable diameter D for use in coronary arteries may range from about 1.5 mm to 4 mm; for carotid arteries, about 5 mm to 10 mm; for saphenous vein, as large as about 4 mm; for aorta, as large as about 2 cm. A suitable diameter for vascular applications in a neurologic setting may range from about 1 mm to 4 mm.

The length L also differs according to the size and shape of the particular anatomical structure to be treated, and according to the size of the treatment site itself. For instance, a length in the range about 5 mm to 40 mm may be employed for use in coronary arteries; for carotid arteries, about 2 cm to 10 cm; for saphenous vein, about 1 cm (for treatment of a focal lesion) to 10 cm; and, in a neurologic setting, about 5 mm to 20 mm.

The thickness of wall 25 differs depending upon the particular material used (especially its strength), and according to the size of the device (especially the diameter) and the radial strength requirements for the particular treatment. The wall thickness can range from about 0.001" (about 0.025 mm), particularly for smaller devices, to about 0.02" (about 0.5 mm), particularly for larger devices.

The cylindrical member 11 is formed of a suitable material acceptable for implantation, as for example in the human body. Suitable such materials include, by way of example, a metal such as a stainless steel, for example 316 stainless or 304 stainless, or a shape memory material such as a nickel-titanium alloy ("nitinol"), or a plastic such as for example a nylon. Suitable such materials also include, by way of example, a composite or laminated material such as for example a platinum/stainless steel laminate or a nitinol/stainless steel laminate or a gold/stainless steel laminate, to provide a combination of materials characteristics.

At the first extremity 24 of cylindrical member 11 is a first end segment 20, and at the second extremity 44 of cylindrical member 11 is a second end segment 40. Between first end segment 20 and second end segment 40 is an expandable, flexible, generally cylindrical intermediate segment 60. Middle segment 60 is formed of a plurality of interlaced ribbon elements or strands, three of which are indicated by way of example at 62 in the Figures, and another three of which are indicated by way of example at 64 (FIG. 1 shows, by way of example, an intermediate segment having in all 18 interlaced strands). As described more fully below, first ends 63 of certain of the strands (62, for example) are attached at attachment points 22 on first end segment 20, and first ends 65 of certain other of the strands (64, for example) are attached at attachment points 42 on second stent segment 40.

Each of first end segment 20 and second end segment 40 can be an expandable stent of any desired configuration.

The particular expandable stent segments 20, 40 shown in an expanded condition by way of example in the figures, have generally longitudinally oriented ribs (for example 21) which are connected generally circumferentially around the cylindrical shape of the stent segment with struts (for example, 23). Such a stent segment can be made according to any of various methods well known in the art, as described in more detail in my copending U.S. patent application Ser. No. 08/818,274 entitled "Stent", filed Mar. 17, 1997, referenced above.

Strands 62, 64 making up the braided intermediate segment 60 preferably are constructed of the same material as the respective first and second segments 20, 40.

The structure of the compound stent according to the invention, as well as the method of making it, may be described with reference to FIGS. 2 and 3. FIGS. 2 and 3 show complementary parts of a compound stent according to the invention which, when assembled as described below, form the compound stent illustrated in FIG. 1.

Thus, in FIG. 2 is shown a first part generally at 14, having a generally cylindrical shape with an outside diameter D about a longitudinal axis 31–31', a length L', and first and second extremities 24, 54. First part 14 includes first end segment 20, which is made up of ribs 21 connected by struts 23, as described above; and strands (for example, 62), each attached by a first end 63 to the first end segment at attachment points 22. As shown in FIG. 2, each of the strands (for example 62) takes a helical course about the longitudinal axis 31–31', so that in the aggregate, the firsts strands (for example 62) conform to the generally tubular configuration of the part 14. The second ends 67 of the first strands, opposite the ends 63 which are attached to the first end segment, 20 are free.

Similarly, in FIG. 3 is shown a second part generally at 16, having a generally cylindrical shape with an outside diameter D about a longitudinal axis 32–32', a length L", and first and second extremities 34, 44. Second part 16 includes second end segment 40, which is made up of ribs 21 connected by struts 23, as described above; and strands (for example, 66), each attached by a first end 65 to the first end segment at attachment points 42. As shown in FIG. 3, each of the second strands (for example 64) takes a helical course about the longitudinal axis 32–32', so that in the aggregate, the second strands (for example 64) conform to the generally tubular configuration of the part 16. The second ends 69 of the first strands opposite the ends 65 which are attached to the second end segment 40 are free.

As noted above, first and second parts 14, 16 are complementary. Where the strands take a helical course, as shown in the Figures, the helices of the first strands turn in the opposite direction from those of the second strand. That is, if the first strands follow a right-hand helical course, the second strands follow a left-hand helical course.

Now, generally cylindrical member 11, shown in FIG. 1, can be constructed by assembling complementary parts 14, 16 in an unexpanded condition, and then causing or inducing or allowing the assembly to expand, as follows. (The complementary parts 14, 16 are shown in an expanded condition in FIGS. 2 and 3 for clarity of illustration with reference to FIG. 1.) Unexpanded parts 14, 16 are positioned so that their respective longitudinal axes 31–31' and 32–32' are aligned, and oriented so that their respective second extremities are apposite. Then parts are moved together along the now common axis 12–12', so that the first strands pass the second strands and the strands are interlaced. When the second extremities of the strands have reached the end segments of the respective complementary pieces, formation of the intermediate segment is complete, and the movement is halted.

Usually the free end of at least one of the first strands and of the second strands (more usually the free ends of two or more, and most usually the free ends of all, of each set of strands) is attached to the respective complementary part. Conveniently, the respective first end attachment points 22, 42 can also serve as attachments points for free ends 67, 69. The attachment can be accomplished for example by spot welding or by mechanical interlock.

The number of strands initially attached to each of the complementary pieces 14, 16 can differ according to the size of the device and the requirements for flexibility and radial strength. The completed intermediate segment should contain a total of at least 8 strands, more usually 12–20, up to as many as 24 strands or more for larger devices. Accordingly, where the complementary parts contribute equal numbers of strands, as may be preferred, each part should initially have at least 4 and more usually 6–10, up to as many as 12 strands.

Where the strands take a helical course, the number of turns of the helix will of course depend in part on the length of the intermediate braid segment of the device. As will be appreciated, however, where the turns of the helix are very short, the expandability of the braid may be limited; and there the turns are very long, the radial strength may be compromised.

Usually the interlacing will result in a regular design; that is to say, a pattern of over-and-under passes will be followed for all the strands. It is not necessary however, that a strict pattern be adhered to, or that all the strands be woven according to the same pattern.

Where the strands are constructed of the same material as the end segments, the strands usually would be about as thick as the ribs or struts of the end segments; usually the thickness of the struts would fall within the range of the wall thickness for a particular device.

Each of the parts 14, 16 can readily be made by techniques known in the art. As noted above, the complementary parts are made and assembled to form the cylindrical member in an unexpanded condition, and the device is caused or induced or allowed to expand at the treatment site within the body. Accordingly, the material from which the part is to be made can be provided in the form of a tube whose outside diameter is the diameter appropriate for the device in the contracted state, and whose wall thickness is as appropriate for the device. Expansion will result in shortening of the intermediate segment, to a readily determinable degree that depends upon, among other things, the particular arrangement of strands and the expansion ratio. (The end segments may shorten as well, depending upon their design; as detailed in my copending U.S. patent application filed Mar. 17, 1997, titled "Stent", referenced above, the particular configuration of ribs and struts in the stent segments 20, 40 shown by way of example in the Figures herein have the advantage that they do not change length when expanded). Accordingly, the length of the tubing from which the parts 14, 16 are made must be longer than the lengths L', L" desired for the parts in their expanded condition in the assembled and expanded device. Usual expansion ratios range to as high as 5:1; that is, the expanded outside diameter can be as much as about 5 times as great as the contracted (unexpanded) diameter. More usually the expansion ratio is about 3:1.

A pattern may be formed in the tubular material which will when the device is expanded result in the forms of the parts 14, 16. The pattern can be formed by use of conventional etching or laser cutting techniques. This process is generally described, with reference to construction of a stent as is shown for example herein to provide the expandable end segments, in my copending U.S. patent application Ser. No. 08/818,274 filed Mar. 17, 1997, entitled "Stent", referenced above.

For ease in handling, the first parts 14 can be made by cutting a first piece of the tubular material, to provide an expandable stent segment at both ends and a set of strands (if helical, then all turning in one direction); and then cutting the resulting piece transversely midway the length of the strands to produce two identical first parts. Similarly, complementary second parts 16 can be made by cutting a second piece of the tubular material to provide an expandable stent segment at both ends and a set of strands (if helical, then all turning in the direction opposite that for the first pieces); and then cutting the resulting piece transversely midway the length of the strands to produce two identical second parts. Then the complementary parts are assembled as described above. As noted above, the braided intermediate segment of the device will shorten as the device is expanded, and each of the pieces of tubing must accordingly have a length sufficient to provide two parts each of which when expanded will have the desired lengths L' or L".

An alternative method for making a device as in FIG. 1 does not employ the assembly of a complementary parts. In this method, a cylindrical member is cut as described above from a piece of the tubular material, to provide an expandable stent segment at both ends and a set of strands (if helical, then all turning in one direction). Then the weaving is performed by passing one or more separate free strands through the resulting multiple spiral according to a desired pattern to produce the desired weave. Where only a single such separate free strand is used, there are only two free ends in the resulting braided intermediate segment, reducing the number of welds or mechanical attachments that must be made in order to remove all the free ends. The separate free strand may be but need not necessarily be of the same material as the cylindrical part. The device will shorten as it expands, and accordingly the length of the tubular material from which the cylindrical member is cut must be correspondingly longer than the desired overall device length L.

The compound stent according to the invention can be deployed in a conventional manner into the desired location. For example it can be deployed on a balloon catheter, by placing the compound stent onto the deflated balloon, using the balloon catheter to carry the compound stent to the desired site, and thereafter inflating the balloon to expand the stent into the desired size, after which the balloon can be deflated and removed. Similarly, if the compound stent is formed of a self-expanding material, the stent can be deployed by use of an appropriate stent deployment catheter, after which the stent can be released to expand to the maximum desired diameter, after which the catheter deployment mechanism can be removed.

What is claimed:

1. A compound stent comprising a cylindrical member having a length and first and second extremities and having a wall defining a central bore extending from said first extremity to said second extremity and having a longitudinal axis, said cylindrical member having first and second end segments and an intermediate segment having first and second ends adjoining said first and second end segments, each of said first and second end segments having a plurality of struts extending in the wall spaced apart of the longitudinal axis and permitting radial expansion of the segment from a contracted position to an expanded condition, means extending in the wall to prevent shrinkage in length of the segment as it is expanded, being comprised of a plurality of longitudinally extending spaced-apart ribs which serve as compression resisting members, each of said ribs extending the length of the segment.

2. The stent of claim 1 wherein said intermediate segment is formed of the same material as the first and second segments.

3. The compound stent of claim 1 wherein said outside diameter when in said expanded condition is in the range about 1 mm to about 2 cm.

4. The compound stent of claim 1 wherein said length when in said expanded condition is in the range about 5 mm to about 10 cm.

5. The compound stent of claim 1 wherein the thickness of said wall is in the range about 0.001" to about 0.02".

6. The compound stent of claim 1 wherein said diameter in said expanded condition is in the range about 1.5 mm to about 4 mm and said length in said expanded condition is in the range about 5 mm to about 4 cm.

7. The compound stent of claim 1 wherein said diameter in said expanded condition is in the range about 5 mm to about 10 mm and said length in said expanded condition is in the range about 2 cm to about 10 cm.

8. The compound stent of claim 1 wherein said diameter in said expanded condition is in the range about 1 mm to about 4 mm and said length in said expanded condition is in the range about 1 cm to about 10 cm.

9. The compound stent of claim 1 wherein said diameter in said expanded condition is in the range about 1 mm to about 4 mm and said length in said expanded condition is in the range about 5 mm to about 20 mm.

10. The compound stent of claim 1 wherein said material comprises a metal.

11. The compound stent of claim 10 wherein said metal comprises a stainless steel.

12. The compound stent of claim 10 wherein said metal comprises a nickel-titanium alloy.

13. The compound stent of claim 1 wherein said material comprises a plastic.

14. The compound stent of claim 1 wherein said braided material comprises a metal.

15. The compound stent of claim 14 wherein said metal comprises a stainless steel.

16. The compound stent of claim 14 wherein said metal comprises a nickel-titanium alloy.

17. The compound stent of claim 14 wherein said material comprises a plastic.

18. The compound stent of claim 1 wherein said material comprises a laminate selected from the group consisting of nitinol/stainless steel laminate, platinum/stainless steel laminate, and gold/stainless steel laminate.

19. The compound stent of claim 1 wherein said intermediate segment comprises a plurality of interlaced strands.

20. The compound stent of claim 19 wherein said strands are of a metal or plastic material.

21. The compound stent of claim 20 wherein said strands are all of the same material.

22. The compound stent of claim 19 wherein said intermediate segment comprises a plurality of strands in a braided arrangement.

23. The compound stent of claim 22 wherein said intermediate segment comprises a braided arrangement of from 8–24 strands.

24. The compound stent of claim 23 wherein said intermediate segment comprises a braided arrangement of from 12–20 strands.

25. The compound stent of claim 19 wherein each of said strands is attached to one of said end segments.

26. The compound stent of claim 19 wherein each of said strands is attached to both of said first and second end segments.

* * * * *